United States Patent
Frantz et al.

(10) Patent No.: US 9,511,007 B2
(45) Date of Patent: Dec. 6, 2016

(54) TEAR FREE BABY CLEANSER

(71) Applicant: BASF SE, Ludwigshafen (DE)

(72) Inventors: Seren Frantz, Gordonsville, VA (US);
Jeffrey Parker, Lumberville, PA (US);
Miroslav Majcen, Philadelphia, PA (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/390,050

(22) PCT Filed: Apr. 22, 2013

(86) PCT No.: PCT/US2013/037576
§ 371 (c)(1),
(2) Date: Oct. 2, 2014

(87) PCT Pub. No.: WO2013/163074
PCT Pub. Date: Oct. 31, 2013

(65) Prior Publication Data
US 2015/0057208 A1 Feb. 26, 2015

Related U.S. Application Data

(60) Provisional application No. 61/636,984, filed on Apr. 23, 2012, provisional application No. 61/787,739, filed on Mar. 15, 2013.

(51) Int. Cl.
| | | |
|---|---|---|
| *C11D 1/825* | (2006.01) | |
| *C11D 3/22* | (2006.01) | |
| *A61Q 5/02* | (2006.01) | |
| *A61Q 19/10* | (2006.01) | |
| *A61K 8/39* | (2006.01) | |
| *A61K 8/73* | (2006.01) | |
| *A61K 8/37* | (2006.01) | |
| *C11D 1/66* | (2006.01) | |
| *C11D 3/37* | (2006.01) | |
| *A61K 8/60* | (2006.01) | |
| *A61Q 19/00* | (2006.01) | |

(52) U.S. Cl.
CPC .............. *A61K 8/375* (2013.01); *A61K 8/39* (2013.01); *A61K 8/604* (2013.01); *A61K 8/73* (2013.01); *A61Q 5/02* (2013.01); *A61Q 19/005* (2013.01); *A61Q 19/10* (2013.01); *C11D 1/662* (2013.01); *C11D 3/3715* (2013.01); *A61K 2800/33* (2013.01); *A61K 2800/75* (2013.01)

(58) Field of Classification Search
CPC ......... C11D 1/662; C11D 1/667; C11D 1/825; C11D 3/2093; C11D 3/22; C11D 3/3715; A61Q 5/02; A61Q 19/10; A61K 8/375; A61K 8/39; A61K 8/73
See application file for complete search history.

(56) References Cited

U.S. PATENT DOCUMENTS

| | | |
|---|---|---|
| 2002/0151446 A1 | 10/2002 | Piterski et al. |
| 2005/0180942 A1* | 8/2005 | Shimizu .................. A61K 8/31 424/70.31 |
| 2008/0261842 A1 | 10/2008 | Hall et al. |
| 2011/0319307 A1 | 12/2011 | Gunn et al. |
| 2012/0027826 A1* | 2/2012 | Strauss et al. ................ 424/401 |
| 2012/0157365 A1 | 6/2012 | Fevola |

FOREIGN PATENT DOCUMENTS

| | | | | |
|---|---|---|---|---|
| EP | 1 374 845 | | 1/2004 | |
| EP | 2 366 376 | | 9/2011 | |
| EP | 2366376 | * | 9/2011 | ............... A61K 8/34 |
| JP | 2005-213237 A | | 8/2005 | |

OTHER PUBLICATIONS

English language abst. of JP 2005-213237 Aug. 11, 2005.
International Search Report dated Jul. 29, 2013.
International Preliminary Report on Patentability dated Oct. 28, 2014.
Written Opinion of the International Searching Authority dated Jul. 29, 2013.

* cited by examiner

Primary Examiner — Brian P Mruk
(74) Attorney, Agent, or Firm — Lowenstein Sandler LLP

(57) ABSTRACT

The present application directed to a unique combination of surfactants in concentrated form. In particular certain combinations of alkyl polyglucosides and polyglyceryl fatty acid esters when combined yield a cleansing concentrate which can be diluted to form tear free or mild cleanser.

12 Claims, No Drawings

TEAR FREE BABY CLEANSER

This application claims the benefit of U.S. Provisional Application No. 61/636,984, filed Apr. 23, 2012 and U.S. Provisional Application No. 61/787,739, filed Mar. 13, 2013 herein incorporated entirely by reference.

FIELD OF THE INVENTION

The present application is directed to a unique combination of surfactants in concentrated form. In particular certain combinations of alkyl polyglucosides and polyglyceryl fatty acid esters when combined yield a cleansing concentrate which can be diluted to form tear free or mild cleanser.

BACKGROUND

Baby skin care and toiletries are important segments of the baby care market. Safety is a necessary pre-requisite of any product sold into this market. In particular, cleansing products for babies and young children need to meet certain non-irritation standards in use. For example, shampoos and skin cleansing formulations could be "tear-free" and non-stinging when the eye becomes exposed to small amounts of the formulation. Of course, baby skin is somewhat more sensitive and delicate than adult skin and should only be exposed to formulations which are mild and non-irritating but still provide the cleansing effect.

There are numerous products on the market which accomplish the "tear-free" requirement. However, many of these contain additional ingredients which are undesired. For example, many contain sulfate surfactants, ethylene oxide and/or polyethylene glycol surfactants.

It would also be very helpful to be able to provide a "tear-free" concentrate (less than 70% water) which may simply be added to manufacturers' individual formulations and upon dilution accomplishes the cleansing effect without ingredients such as sulfate, ethylene oxide and/or polyethylene glycol surfactants.

Additionally it would be a great advantage to provide a high concentrate blend of surfactants which is clear and of low viscosity.

SUMMARY OF THE INVENTION

A cleansing concentrate, preferably a clear concentrate comprising
- a) about 5 to about 30, preferably about 10 to about 25, most preferably about 12 to about 18 wt. % polyglycerine partial esters, wherein the partial esters are $C_8$ to $C_{22}$, especially $C_8$ to $C_{10}$ partial esters;
- b) about 20 to about 60, preferably 25 to about 50, most preferably about 28 to about 42 wt. % alkyl polyglucoside;
- c) optionally, about 0.5 to about 4 wt. % preservative; and
- d) optionally, a pH adjusting compound, with the proviso that the concentrate contains less than 70, preferably less than 60, and more preferably less than 50 and especially less than 45 wt. percent water and weight percent is based on the total weight of the concentrate.

The concentrate when diluted forms a shampoo or skin wash which gives a product which is tear-free determined by standard ophthalmologic testing.

One of the primary advantages of this highly concentrated surfactant blend is it is clear and of low viscosity. By high concentration we mean less than 60 percent water, preferably less than 50 and most preferably less than 45 wt. % water. This would give a solid concentration of greater than 40 percent, greater than 50 percent or greater than 65 percent solids. The solids refers to any component other than water.

Further the concentrate is a specific blend of non-irritating surfactants suitable for use in cleansing for babies or children or adults with sensitive skin.

Thus the invention is also directed to method of reducing the irritancy to eyes of a personal cleansing formula, especially a shampoo by adding thereto nonionic surfactants defined by a) and b), wherein
- a) at least 1 to about 8 wt. %, preferably about 1.5 to about 5 wt. % polyglycerol partial ester,
- b) about 8 to about 20 wt. %, preferably about 10 to about 16 wt % of alkyl polyglucoside, wherein the wt. % is based on the total weight of the personal cleansing formulation and the partial esters are $C_8$ to $C_{22}$.

DETAILED DESCRIPTION OF THE INVENTION

The "concentrate" for purposes of this invention means a concentrated stable dispersion of surfactants in water, wherein the concentration of the nonionic surfactants exceeds 30, 40, 50 or 55 wt. % based on the total weight of the concentrate.

The concentrate is of relatively low viscosity which makes its use in formulations easy.

The concentrate viscosity will vary but should not exceed 10,000 cps. More preferably the concentrate will have a viscosity of less than 5,000 cps, more preferably less than 2500 cps, and most preferably less than 1200 cps. Accordingly, the viscosity of the concentrate will vary from about 1200 cps to about 10,000 cps.

The viscosity is measured using Brookfield RVT spindle #4, 20 RPM.

Dilution of this concentrate can yield a tear-free or reduced-tears cleansing system that is mild enough to be used on babies. In one instance, the concentrate is sulfate-free. In one instance, the baby cleansing system is sulfate free. In one instance the concentrate is EO/PO free. In one instance the baby cleansing system is ethylene oxide/polypropylene oxide (EO/PO) free.

Accordingly, preferably the concentrate is sulfate free. Most preferably the concentrate is sulfate free and EO/PO free, especially, sulfate free, EO/PO and polyethylene glycol (PEG) free.

Other typical ingredients may be added to the concentrate but the concentrate will contain both ingredients a) and b).

When the phrase "personal cleansing formulation" is used what is meant is not the "concentrate" but the final shampoo or body wash formulation. Thus the wt. percent of a) and b) will necessarily be less in the final personal cleansing formulation. For example, component a) will normally range from about 1 to about 8 wt. %, preferably about 1.5 to about 5 wt. % polyglycerol partial ester and about 8 to about 20 wt. %, preferably about 10 to about 16 wt %.

The "concentrate" wt. % for a) will range from about 5 to about 30, preferably about 10 to about 25, most preferably about 12 to about 18 wt. % for the polyglycerine partial esters and the wt. % for b) will range from about 20 to about 60, preferably 25 to about 50, most preferably about 28 to about 42 wt. % for the alkyl polyglucoside.

Polyglycerine Partial Esters

Polyglycerol partial esters are obtainable by reacting polyglycerols or a single glycerol with linear or branched fatty acids having 6 to 22 carbon atoms. The polyglycerol mixture used advantageously has an average degree of condensation of from 2 to 12, preferably 2 to 10.

The degree of esterification of the polyglyrol mixture is for example between 5 and 70%, preferably between 10 and 30% based on the hydroxyl groups of the condensed glycerol.

Of particular interest are $C_8$-$C_{18}$ polyglyceryl monoesters. For example, polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and combinations of two or more thereof.

Of particular interest are $C_8$-$C_{18}$ polyglyceryl partial esters. For example, polyglyceryl-4 caprylate/caprate, polyglyceryl-10 caprylate/caprate, polyglyceryl-4 caprate and especially polyglyceryl-10 caprylate/caprate.

Alkyl Polyglucoside

Alkyl polyglucosides (APGs) are well known in the art and may be purchased under the tradename Plantaren® from BASF SE.

The terms alkyl polyglucoside and alkyl glucoside are interchangeable.

An alkyl polyglycoside is formed from the reaction of glucose and fatty alcohol. An alkyl polyglycoside compound has a hydrophobic portion (carbon chain) and a hydrophilic portion (glycoside unit or group). When describing an alkyl polyglycoside, the average degree of polymerization (DP) is mentioned. For example, in an alkyl polglycoside or alkyl glycoside a compound with a DP of about 1.4, there are, on average, 1.4 units of glucose for each alkyl group. An alkyl polyglucoside or alkyl glucoside is normally a mixture of varying amounts of glucose units on the molecule. It is to be understood that a DP of 1.4 does not mean that each molecule has 1.4 glucose units.

Alkyl polyglucosides may be represented by the following general formula: $R_1$—O—$(R_2O)_b$-$(Z)_a$ wherein $R_1$ is a monovalent organic radical having from about 6 to about 30 carbon atoms, $R_2$ is a divalent alkylene radical having from 2 to 4 carbon atoms, and Z is a saccharide residue having 5 or 6 carbon atoms, b is a number from 0 to about 12, and a is a number of from 1 to 6.

Additional suitable alkyl polyglucosides include, but are not limited to GLUCOPON® 225DK, in which the alkyl group contains 8 to 10 carbon atoms and has an average DP of 1.7; GLUCOPON® 625UP, in which the alkyl group has 12 to 16 carbon atoms and has an average DP of 1.6; APG® 325N, in which the alkyl group has 9 to 11 carbon atoms and has an average DP of 1.5; GLUCOPON® 600UP, in which the alkyl group has 12 to 16 carbon atoms and has an average DP of 1.4; PLANTAREN 2000®, in which the alkyl group has 8 to 16 carbon atoms and has an average DP of 1.5; and PLANTAREN 1300®, in which the alkyl group has 12 to 16 carbon atoms and an average DP of 1.6.

The alkyl polyglucosides is typically formed by reacting a sugar with a higher alcohol in the presence of an acid catalyst, or by reacting a sugar with a lower alcohol (for example, methanol, ethanol, propanol, butanol) to thereby provide a lower alkyl glycoside, which is then reacted with a higher alcohol. The higher alcohol generally has the formulation $R_1O(R_2O)_xH$, wherein $R_1$ represents a straight or branched alkyl or alkenyl group having from 8 to 22 carbon atoms, $R_2$ represents an alkylene group having from 2 to 20 carbon atoms, and x is a mean value that is 0 to 10.

Specific non-limiting examples of the higher alcohol are straight or branched alkanol such as hexanol, heptanol, octanol, nonanol, decanol, dodecanol, tridecanol, tetradecanol, pentadecanol, hexadecanol, heptadecanol, octadecanol, methylpentanol, methylhexanol, methylheptanol, methyloctanol, methyldecanol, methylundecanol, methyltridecanol, methylheptadecanol, ethylhexanol, ethyloctanol, ethyldecanol, ethyldodecanol, 2-heptanol, 2-nonanol, 2-undecanol, 2-tridecanol, 2-pentadecanol, 2-heptadecanol, 2-butyloctanol, 2-hexyloctanol, 2-octyloctanol, 2-hexyldecanol and/or 2-octyldecanol; an alkenol such as hexenol, heptenol, octenol, nonenol, decenol, undecenol, dodecenol, tridecenol, tetradecenol, pentadecenol, hexadecenol, heptadecenol and octadecenol. These alcohols may be used either alone or a mixture of two or more of them.

Preferred alkyl glucosides comprise from about 1 to about 6 glucose residues per molecule, preferably 1 to 4. A preferred glucoside is decyl glucoside, which is the condensation product of decyl alcohol with a glucose polymer or single glucose residue and is available commercially from BASF Corporation of Florham Park, N.J. under the trade name, Plantaren®. Other preferred examples include lauryl glucoside, decyl glucoside and mixtures thereof.

Hydrophobic Emollients

Advantageously the concentrate may also contain in addition to components a), b), c) and d) a component e) a hydrophobic emollients.

The hydrophobic emollients of interest are esters of fatty (carboxylic) acids. The fatty acid portion may have a carbon chain length from about $C_{12-30}$. The term $C_{12-30}$ carboxylic acid is meant to comprise pure acids or mixtures thereof. The carbon chain may be linear or branched; saturated or unsaturated (i.e., having one or more double bonds). The fatty acid component may also contain one or more, e.g. two, hydroxy groups. These acids comprise the so-called fatty acids, i.e. acids derived from naturally occurring fats.

Particularly preferred hydrophobic emollients are esters of fatty acids and glycerol. In one embodiment, the hydrophobic emollient is a triglyceride, but, in certain embodiments, the composition is free of triglycerides. In a preferred embodiment the hydrophobic emollient is a mono- or diglyceride, such as a $C_{12-30}$ mono- or diglyceride or a mixture thereof, such as linear, saturated $C_{12-30}$ mono- or diglyceride. The quantity of mono- and/or diglyceride in such mixture may vary, it can be between 0 and 100%.

Preferred are mixtures that contain more than 50% of monoglyceride, in particular more than 70% of the latter. Of particular note are compositions in which the ester of glycerol and fatty acid is at least 80%, in particular at least 90%, more in particular at least 95% or even at least 99% of $C_{12-30}$ carboxylic acid monoglyceride.

In one embodiment, the diglyceride includes two different carboxylic acid. These mixed diglycerides also comprise (mono-$C_{12-30}$ carboxylic acid) (mono-oleic acid) glycerides. An example thereof is (mono-palmitoleic acid) (mono-oleic acid) glyceride.

Preferably the carboxylic acid has from about 16 to about 22 carbon atoms, more preferably from about 16 to about 20 carbon atoms, still more preferably from about 16 to about 18 carbon atoms. Of particular interest are those containing 18 carbon atoms. A particularly preferred ester of glycerol and fatty acid is glyceryl mono- or dioleate. One particularly preferred ester of glycerol and fatty acid that has excellent mildness and skin-feel is a glyceryl monooleate (HLB of approximately 3.8) that is commercially available from BASF Corporation, Florham Park, N.J. and sold under the trademark LAMESOFT PO 65, a mixture of about 31% glycerol monooleate that is blended with $C_8$-$C_{18}$ coco glucoside and water. LAMESOFT PO 65 is sometimes referred to as a lip layer enhancer.

The hydrophobic emollient is different than component a). For example, the hydrophobic emollient is typically a >=C16 fatty acid esters of glycerol.

Compositions of the present invention comprise at least one monoglyceride with 12 to 22 C atoms in the fatty acid moiety. The fatty acid moiety can be saturated or unsaturated with 1 to 3 ethylenic bonds. Preferred monoglycerides are with 14 to 18 and most preferred are with 16 to 18 C atoms in fatty acid moiety. Non-limiting examples to suitable monoglycerides suitable for the compositions of the present invention are glyceryl monolaurate, glyceryl mono myristate, glyceryl mono stearate, glyceryl mono behenate, glyceryl mono palmitate, glyceryl mono palmitoleate, glyceryl mono oleate, glyceryl mono linolate and their mixtures. Preferred ones are gylceryl stearate, glyceryl oleate, glyceryl palmitate, glyceryl mono palmitoleate, glyceryl mono linolate and their mixtures.

Concentration of the monogylceride in the cleansing concentrate of the present invention ranges from 0.01 to 5%, preferably 0.05 to 3%, more preferably 0.1 to 2.5% and most preferably 0.25 to 2% by weight calculated on the basis of the total concentrate.

Further emollients such as coco glycerides make an excellent addition to the personal cleansing formulation (shampoo or body wash). Such products under the trademet Myritol® 331 can be purchased from BASF Corporation, Florham Park, N.J. Typical amounts in the personal cleansing formulation may vary from about 0.5 to about 3 wt. % of the personal cleansing formulation.

Accordingly the claimed cleansing concentrate preferably a clear concentrate comprises
- a) about 5 to about 30, preferably about 10 to about 25, most preferably about 12 to about 18 wt. % polyglycerine partial esters, wherein the partial esters are $C_8$ to $C_{22}$, especially $C_8$ to $C_{10}$ partial esters;
- b) about 20 to about 60, preferably 25 to about 50, most preferably about 28 to about 42 wt. % alkyl polyglucoside;
- c) optionally, about 0.5 to about 4 wt. % preservative; and
- d) optionally, a pH adjusting compound, with the proviso that the concentrate contains less than 70, preferably less than 60, and more preferably less than 50 and especially less than 45 wt. percent water and weight percent is based on the total weight of the concentrate.

A preferred embodiment of the above cleansing concentrate comprises
- a) about 5 to about 30, preferably about 10 to about 25, most preferably about 12 to about 18 wt. % polyglycerine partial esters, wherein the partial esters are selected from the group consisting of polyglyceryl-4 caprylate/caprate, polyglyceryl-10 caprylate/caprate and polyglyceryl-4 caprate and especially polyglyceryl-10 caprylate/caprate.
- b) about 20 to about 60, preferably 25 to about 50, most preferably about 28 to about 42 wt. % alkyl polyglucoside;
- c) optionally about 0.5 to about 4 wt. % preservative; and
- d) optionally, a pH adjusting compound, with the proviso that the concentrate contains less than 70, preferably less than 60, and more preferably less than 50 and especially less than 45 wt. percent water and weight percent is based on the total weight of the concentrate.

A second preferred embodiment of the above cleansing concentrate comprises
- a) about 5 to about 30, preferably about 10 to about 25, most preferably about 12 to about 18 wt. % polyglycerine partial esters, wherein the partial esters are selected from the group consisting of polyglyceryl-4 caprylate/caprate, polyglyceryl-10 caprylate/caprate and polyglyceryl-4 caprate and especially polyglyceryl-10 caprylate/caprate.
- b) about 20 to about 60, preferably 25 to about 50, most preferably about 28 to about 42 wt. % alkyl polyglucoside, wherein the alkyl of the alkyl polyglucoside is a $C_8$ to $C_{16}$ alkyl group and the glucoside has an average degree of polymerization ranging from about 1 to 4, most preferably 1 to 3, especially 1 to 2;
- c) optionally about 0.5 to about 4 wt. % preservative; and
- d) optionally, a pH adjusting compound.

A third preferred embodiment of the above cleansing concentrate comprises
- a) about 5 to about 30, preferably about 10 to about 25, most preferably about 12 to about 18 wt. % polyglycerine partial esters, wherein the partial esters are selected from the group consisting of polyglyceryl-4 caprylate/caprate, polyglyceryl-10 caprylate/caprate and polyglyceryl-4 caprate and especially polyglyceryl-10 caprylate/caprate;
- b) about 20 to about 60, preferably 25 to about 50, most preferably about 28 to about 42 wt. % alkyl polyglucoside, wherein the alkyl of the alkyl polyglucoside is a $C_8$ to $C_{16}$ alkyl group and the glucoside has an average degree of polymerization ranging from about 1 to 4, most preferably 1 to 3, especially 1 to 2;
- c) optionally about 0.5 to about 4 wt. % preservative;
- d) optionally, a pH adjusting compound; and
- e) about hydrophobic emollient comprising an fatty acids esters of glycerol different from component a).

A further preferred embodiment of the above cleansing concentrate comprises
- a) about 5 to about 30, preferably about 10 to about 25, most preferably about 12 to about 18 wt. % polyglycerine partial esters, wherein the partial esters are selected from the group consisting of polyglyceryl-4 caprylate/caprate, polyglyceryl-10 caprylate/caprate and polyglyceryl-4 caprate and especially polyglyceryl-10 caprylate/caprate;
- b) about 20 to about 60, preferably 25 to about 50, most preferably about 28 to about 42 wt. % alkyl polyglucoside, wherein the alkyl of the alkyl polyglucoside is a $C_8$ to $C_{16}$ alkyl group and the glucoside has an average degree of polymerization ranging from about 1 to 4, most preferably 1 to 3, especially 1 to 2;
- c) optionally about 0.5 to about 4 wt. % preservative;
- d) optionally, a pH adjusting compound; and
- e) about 0.01 to 5 wt. % of a hydrophobic emollient comprising a >=C16 fatty acid ester of glycerol with the proviso that e) is different from component a).

A most preferred cleansing concentrate comprises
- a) about 5 to about 30, preferably about 10 to about 25, most preferably about 12 to about 18 wt. % polyglycerine partial esters, wherein the partial esters are selected from the group consisting of polyglyceryl-4 caprylate/caprate, polyglyceryl-10 caprylate/caprate and polyglyceryl-4 caprate and especially polyglyceryl-10 caprylate/caprate;

b) about 20 to about 60, preferably 25 to about 50, most preferably about 28 to about 42 wt. % alkyl polyglucoside, wherein the alkyl of the alkyl polyglucoside is a $C_8$ to $C_{16}$ alkyl group and the glucoside has an average degree of polymerization ranging from about 1 to 4, most preferably 1 to 3, especially 1 to 2;

c) optionally about 0.5 to about 4 wt. % preservative;

d) optionally, a pH adjusting compound; and e) about 0.01 to 5 wt. % of a hydrophobic emollient is a monoglycerides selected from the group consisting of glyceryl monolaurate, glyceryl mono myristate, glyceryl mono stearate, glyceryl mono behenate, glyceryl mono palmitate, glyceryl mono palmitoleate, glyceryl mono oleate, glyceryl mono linolate and mixtures thereof, preferably gylceryl stearate, glyceryl mono oleate, glyceryl palmitate, glyceryl mono palmitoleate, glyceryl mono linolate and mixtures thereof, and most preferably glyceryl mono oleate.

As mentioned previously the invention is also directed to a method of reducing the irritancy to eyes of a personal cleansing formulation, especially a shampoo by adding thereto nonionic surfactants defined by a) and b), wherein a) at least 1 to about 8 wt. %, preferably about 1.5 to about 5 wt. % polyglycerol partial ester, b) about 8 to about 20 wt. %, preferably about 10 to about 16 wt % of alkyl polyglucoside, wherein the wt. % is based on the total weight of the personal cleansing formulation and the partial esters are $C_8$ to $C_{22}$.

A preferred embodiment of this method is the final formulation of the personal cleansing formulation comprises no further nonionic surfactants or anionic surfactants.

Use

The concentrate when diluted may be used to form a shampoo or skin wash giving a product which is tear-free determined by standard ophthalmologic testing. The formulated shampoo or skin wash (after addition of the concentrate) may be in basically any form such as a gel, liquid, paste or solid. The concentrate cam be diluted to wet a wipe or nonwoven used for cleansing.

The concentrate might also be applied to washing of pets, facial cleansers, sensitive skin formulations and the like. The concentrates would be appropriate for formulating children and baby products as well as for sensitive adults.

EXAMPLES

Concentrate Formulations

Example 1

| INGREDIENTS | INCI NAME | wt % | % Surfactant |
|---|---|---|---|
| Polyaldo 10-1-CC KFG | Polyglyceryl-10 Caprylate/Caprate | 12.76 | 12.8 |
| Plantaren ® 2000N UP (~50% active) | Decyl Glucoside | 76.56 | 38.3 |
| Lamesoft ® PO 65 (~65% active) | Coco Glucoside (and) Glyceryl Oleate | 7.64 | 5 |
| Sodium Benzoate | Sodium Benzoate | 1.50 | |
| Citric Acid (100%) | Citric Acid | 1.54 | |
| | | 100% by wt | 56.1% surfactants |
| Appearance | | Clear, pale yellow | |
| pH | | 5.4 | |
| Viscosity (RVT 4/20 RPM) | | 1,040 cps | |

Example 2

| INGREDIENTS | INCI NAME | wt % | % Surfactant |
|---|---|---|---|
| Polyaldo 10-1-CC KFG | Polyglyceryl-10 Caprylate/Caprate | 12.8 | 12.8 |
| Plantaren ® 2000N UP | Decyl Glucoside | 77.0 | 38.5 |
| Lamesoft ® PO 65 | Coco Glucoside (and) Glyceryl Oleate | 7.7 | 5.0 |
| NaOH (20%) | Water (and) Sodium Hydroxide | 4.5 | |
| | | 100% by wt | 56.3% surfactants |
| Appearance | | Clear, golden yellow | |
| pH | | 11.91 | |
| Viscosity (RVT 4/20 RPM) | | 1,250 cP | |

Diluted Concentrates in Baby Wash

About 18 to 20% of the above concentrate (Example 1) is added to approximately 78 to 80 wt. % water to make a baby wash formulation.

Example 3

| INGREDIENTS | INCI NAME | US-00813-207A wt % | US-00813-207B wt % | US-00813-207C wt % |
|---|---|---|---|---|
| DI Water | Water | 79.05 | 76.55 | 77.30 |
| Natrasol Plus 330CS | Cetyl Hydroxyethylcellulose | 0.10 | 0.10 | 0.10 |
| Keltrol CG-SFT | Xanthan Gum | 1.00 | 1.00 | 1.00 |
| US-00842-125 | Decyl Glucoside (and) Polyglyceryl-10 Caprylate/Caprate (and) Coco Glucoside (and) Glyceryl Oleate | 0 | 19.6 | 19.6 |
| Plantaren ® 2000N UP | Decyl Glucoside | 15.00 | 0 | 0 |
| Lamesoft ® PO 65 | Coco Glucoside (and) Glyceryl Oleate | 1.50 | 0 | 0 |
| Sulfopon ® 1216G | Sodium Coco-Sulfate | 0.75 | 0.75 | 0 |
| Myritol ® 331 | Cocoglycerides | 1.50 | 1.50 | 1.50 |
| Sodium Benzoate | Sodium Benzoate | 0.50 | 0.20 | 0.20 |

-continued

| INGREDIENTS | INCI NAME | US-00813-207A wt % | US-00813-207B wt % | US-00813-207C wt % |
|---|---|---|---|---|
| Citric acid (100%) | Citric Acid | 0.60 | 0.30 | 0.30 |
| pH | | 4.48 | 4.54 | 4.54 |
| Viscosity (4/20) | | 2,760 cP | 2,850 cP | 2,910 cP |
| % Solids | | 12.82 | 15.20 | 14.91 |

The shampoo formulation is tested for ophthalmic irritancy by the standard method described below.

Healthy subjects are treated with a 10% solution of the product in sterile water. The 10% solution is poured over the front of the face (slightly laid back) of the volunteers. The subjects kept eyes open during the treatment to ensure eye contact of the solution. Any visible tearing is recorded during the study. After drying, the volunteers are questioned about the experience with regard to discomfort, like stinging, burning, itching and/or tearing eyes. Subsequently, the eye and general eye region were visually inspected and by an eye-ground slit-lamp microscope, by a supervising ophthalmologist for any signs of irritation.

Results

None of the subjects showed any reaction to the test product in the form of tears and there was no report of discomfort in the form of stinging, burning or itching and hence no hint of an irritative effect of the test products US-00813-207B and US-00813-207C. This was confirmed by the ophthalmological examination. Nor were there any signs of eye-lid irritation detected in any of the subjects after the treatment.

Formulations A, B and C all are tear-free. However, only B and C are non-stinging. The difference between A and the B and C formulations is the B and C both contain polyglycerol partial ester (Polyglyceryl-10 Caprylate/Caprate) which appears to provide some sting protection.

The invention claimed is:

1. A cleansing concentrate comprising a stable dispersion of surfactants in water, the dispersion including nonionic surfactants in an amount that exceeds 40 wt. % and that comprises
   a) about 10 to about 25 wt. % polyglycerine partial esters, wherein the partial esters are $C_8$ to $C_{22}$;
   b) about 25 to about 50 wt. % alkyl polyglucoside; and
   c) a hydrophobic emollient that is a fatty acid ester of glycerin that is different than component a), wherein the fatty acid ester of glycerin is a mono ester of glycerin selected from the group consisting of glyceryl mono laurate, glyceryl mono myristate, glyceryl mono stearate, glyceryl mono behenate, glyceryl mono palmitate, glyceryl mono palmitoleate, glyceryl mono oleate, glyceryl mono linolate, and mixtures thereof;
   with the proviso that the concentrate contains less than 70 wt. % water and all weight percents are based on a total weight of the concentrate.

2. The cleansing concentrate according to claim 1, wherein the polyglycerine partial esters are selected from the group consisting of polyglyceryl-4 caprylate/caprate, polyglyceryl-10 caprylate/caprate and polyglyceryl-4 caprate.

3. The cleansing concentrate according to claim 1, wherein the alkyl of the alkyl polyglucoside is a $C_8$ to $C_{16}$ alkyl group, and, wherein the polyglucoside of the alkyl polyglucoside has an average degree of polymerization ranging from about 1 to 4.

4. A method of producing a personal cleansing formula that results in reduced irritancy to an individual's eyes when the personal cleansing formula comes into contact therewith, the method comprising adding nonionic surfactants in an amount that exceeds 40 wt. % to a composition that comprises
   a) about 10 to about 25 wt. % polyglycerol partial ester;
   b) about 25 to 50 wt. % of alkyl polyglucoside; and
   c) a hydrophobic emollient that is a fatty acid ester of glycerin that is different than component a), wherein the fatty acid ester of glycerin is a mono ester of glycerin selected from the group consisting of glyceryl mono laurate, glyceryl mono myristate, glyceryl mono stearate, glyceryl mono behenate, glyceryl mono palmitate, glyceryl mono palmitoleate, glyceryl mono oleate, glyceryl mono linolate, and mixtures thereof;
   wherein the wt. % is based on the total weight of the personal cleansing formulation and the partial esters are $C_8$ to $C_{22}$.

5. The method according to claim 4, wherein the personal cleansing formulation comprises no additional surfactants other than the polyglycerol partial ester and the alkyl polyglucoside.

6. The method according to claim 4, wherein the polyglycerol partial esters are selected from the group consisting of polyglyceryl-4 caprylate/caprate, polyglyceryl-10 caprylate/caprate and polyglyceryl-4 caprate.

7. The method according to claim 4, wherein the alkyl of the alkyl polyglucoside is a $C_8$ to $C_{16}$ alkyl group, and wherein the glucoside of the alkyl polyglucoside has an average degree of polymerization ranging from about 1 to 4.

8. The method according to claim 4 wherein the alkyl polyglucoside is decyl glucoside.

9. The method according to claim 4, further comprising: diluting the personal cleansing formula with an aqueous solution to produce a baby wash formulation.

10. The method according to claim 9, wherein the personal cleansing formula is diluted with the aqueous solution such that an amount of the personal cleansing formula accounts for about 18 to 20 wt % of a total weight of the baby wash formulation.

11. A baby wash formulation formed according to a method comprising:
   diluting the cleansing concentrate of claim 1 with an aqueous solution.

12. The baby wash according to claim 11, wherein the cleansing concentrate is diluted with the aqueous solution such that an amount of the cleansing concentrate accounts for about 18 to 20 wt % of a total weight of the baby wash formulation.

* * * * *